United States Patent
Chen et al.

(10) Patent No.: US 10,688,029 B1
(45) Date of Patent: Jun. 23, 2020

(54) FORMULATION PREPARATION TO TREAT MATURE SKIN FOR RESTORING MOISTURE AND RETARDING AGING PROCESS

(71) Applicant: DermSolace Biotechnology LLC, Hayward, CA (US)

(72) Inventors: Wen Ching Chen, Hayward, CA (US); Shu Chen Wang, Hayward, CA (US); Bryant Chen, Hayward, CA (US); Hanafi Tanojo, Hayward, CA (US)

(73) Assignee: DERMSOLACE BIOTECHNOLOGY LLC, Hayward, CA (US)

( * ) Notice: Subject to any disclaimer, the term of this patent is extended or adjusted under 35 U.S.C. 154(b) by 0 days.

(21) Appl. No.: 16/032,573

(22) Filed: Jul. 11, 2018

(51) Int. Cl.
| | | |
|---|---|---|
| *A61K 8/20* | (2006.01) | |
| *A61K 8/36* | (2006.01) | |
| *A61K 8/44* | (2006.01) | |
| *A61K 8/34* | (2006.01) | |
| *A61K 8/04* | (2006.01) | |
| *A61Q 19/08* | (2006.01) | |
| *A61Q 19/00* | (2006.01) | |
| *A61K 8/06* | (2006.01) | |

(52) U.S. Cl.
CPC .............. *A61K 8/361* (2013.01); *A61K 8/042* (2013.01); *A61K 8/064* (2013.01); *A61K 8/20* (2013.01); *A61K 8/345* (2013.01); *A61K 8/44* (2013.01); *A61Q 19/007* (2013.01); *A61Q 19/08* (2013.01); *A61K 2800/591* (2013.01)

(58) Field of Classification Search
CPC ...... A61K 9/0014; A61K 9/107; A61K 9/143; A61K 9/146; A61K 47/02; A61K 47/10; A61K 47/18; A61K 33/14
See application file for complete search history.

(56) References Cited

U.S. PATENT DOCUMENTS

| | | | | |
|---|---|---|---|---|
| 4,743,442 A | * | 5/1988 | Raaf | A61K 8/0212 424/47 |
| 7,300,649 B2 | * | 11/2007 | Tanojo | A61K 8/19 424/678 |
| 2005/0019285 A1 | * | 1/2005 | Lee | A61K 8/19 424/63 |

OTHER PUBLICATIONS

Stark et al. (J. Biol. Chem.1960;235:3177-3181) (Year: 1960).*
Heinrich et al. (Fundamentals of Pharmacognosy and Phytotherapy E-Book. 2012, Elsevier Health Sciences, p. 293). (Year: 2012) 1 page.*
Olsen et al. (Acta Derm Venereol 1993;73:404-406) (Year: 1993).*
Williams, S.D. Chemistry and Technology of the Cosmetics and Toiletries Industry Springer Science & Business Media 1996 pp. 123-124; 2 pages). (Year: 1996).*
Glyceryl Stearate the Dermatological Review [online] retrieved from: https://thedermreview.com/glyceryl-stearate/; Sep. 28, 2018 6 pages. (Year: 2018).*

* cited by examiner

*Primary Examiner* — Ernst V Arnold
(74) *Attorney, Agent, or Firm* — Squire Patton Boggs (US) LLP

(57) ABSTRACT

Compositions, kits and methods are provided for restoring moisture and retarding the aging process in mature skin. In general, ions, combined amino acids, fatty acids and polyols are included in a physiologically acceptable medium. The compositions, kits and methods can be used as cosmetics, cosmeceuticals or pharmaceuticals for improving mature skin condition, and preventing or treating the aging process and/or lack of moisture.

7 Claims, No Drawings

FORMULATION PREPARATION TO TREAT MATURE SKIN FOR RESTORING MOISTURE AND RETARDING AGING PROCESS

BACKGROUND OF THE INVENTION

The uppermost layer of the skin, called epidermis, is always in a state of self-regeneration. At the bottom layer, keratinocyte stem cells divide into daughter cells, which are displaced outward, and which differentiate through successive overlying layers to enter the stratum corneum. Then, the keratinocytes die (apoptosis) and their cellular organella and cytoplasm disappear during the final process of differentiation. Intercellular lipids are primarily generated from exocytosis of lipid-containing granules called lamellar bodies, during the terminal differentiation. There must be a balance between the dying and newly formed keratinocytes, so the skin will constantly be in optimal state of health. Pugliese (2005) Advanced Professional Skin Care. 3-10.

Ionic signals play important role in the homeostatic mechanism of the epidermal barrier function. In normal skin, calcium is localized with high concentration in the epidermal granular layer, i.e., the uppermost layer of the epidermis, just below the stratum corneum. In keratinocytes, the extracellular level is maintained in a specific equilibrium with the intracellular concentrations. Tanojo et al. (2009) In: Handbook of Cosmetic Science and Technology (eds. A. O. Barel, M. Paye, H. I. Maibach), pp 173-182.

The skin serves numerous functions but its primary function is as a protective layer or barrier. The most important role of the skin for terrestrial animals is to protect the water-rich internal organs from the dry environment. This cutaneous barrier function of the skin resides in the upper most thin layer (approximately 10-20 μm in humans) called stratum corneum. The water impermeability of this layer is 1000 times-high than that of other membranes of living organisms. Wester & Maibach (1995) In: Percutaneous Penetration Enhancers. pp. 21-28.

In summary, combination of ions and some natural materials play an important role in the homeostasis of skin cells and the proper regeneration. A change in the barrier will change the calcium ion gradient in skin and lead to barrier repair process. A severe change might lead to a high degree of calcium signaling, which may induce the activation of various processes, from increased synthesis of skin components or messengers to the inflammatory reactions. Thus, there exists a need for compositions and methods for activating the barrier repair process to restore normal barrier function to skin adversely affected by environmental elements or pathological conditions.

SUMMARY OF THE INVENTION

Compositions, kits and methods are provided for restoring moisture and retarding the aging process for mature skin. The present invention includes a combination of materials that will help the skin to regulate the regeneration and control the water homeostasis. The compositions, kits and methods can be used as cosmetics, cosmeceuticals or pharmaceuticals for improving mature skin condition, and preventing or treating the aging process and lack of moisture.

DETAILED DESCRIPTION OF EMBODIMENTS

While embodiments in accordance with aspects of the present invention are shown and described herein, it will be obvious to those skilled in the art that such embodiments are provided by way of example only. Numerous variations, changes, and substitutions will now occur to those skilled in the art without departing from the scope or spirit of the invention. It should be understood that various alternatives to the embodiments of aspects of the invention described herein may be employed in practicing aspects of the invention. It is intended that the following claims define the scope of the invention and that methods and structures within the scope of these claims and their equivalents be covered thereby.

Aspects of the present invention provide innovative compositions and methods for treating mature skin to prevent aging. These aspects are based on fundamental understanding of the influences some materials have in the regeneration of skin cells and proper repair of skin tissues in maintaining proper skin quality.

It is known that the limited amount of ions in skin enables the skin cells to control the regeneration, and that the presence of natural materials can enhance the skin maturation. Hence, the inventors believe that the application of such combination is essential to achieve the desired compared to the individual applications.

According to aspects of the present invention, compositions and methods are provided for skin care, including prevention or treatment of abnormal skin conditions due to compromised skin barrier function, such as dehydration and wrinkle formation. Without being bound to the particular theory or mechanism of action, the compositions are believed to exert their beneficial effects to the skin through: i) maintaining the balance of major ions in skin with the natural materials; and ii) restoring the balance of the major ions in skin, and the natural materials such as amino acids and fatty acids.

By restoring the balance of major ions and natural materials in the skin, various beneficial effects can be achieved. As skin receives various challenges from the environment and changes in diet, it tries to adapt by adjusting the quality of the skin barrier. When the environment becomes dry, the skin may create a stiff barrier to prevent high level of water loss. The stiff barrier can later result in rough and dull skin. The restoration of ion and material balance will induce the regeneration of normal skin barrier layer, which has the optimum barrier formation and healthy skin. The formation of a normal skin barrier can also ensure the healthy growth of other cells and components of the skin, such as lymphocytes and keratinocytes, thereby achieving optimum skin conditions.

In one aspect of the invention, a composition for skin care is provided. In one embodiment the composition comprises about 0.05-3% w/w of ions such as sodium, calcium, magnesium, based on the total weight of the composition in a physiologically acceptable medium, and in the presence of about 0.05-3% of combined amino acids and about 0.05-3% of fatty acids, with 0.1-5% polyols.

According to embodiments, the compositions include ions, amino acids, fatty acids and polyols at a proper ratio in order to maintain the balance of ions in the skin barrier.

In a particular embodiment, ions, such as sodium, calcium, and magnesium ions are preferred, while potassium and zinc can also be added. The aqueous liquid medium constitutes an aqueous phase, which may be the continuous phase of the composition.

The amino acids can be provided from the plant or animal sources, such as collagen amino acids, or silk amino acids. Natural or modified amino acids, such as arginine, cystine, glutamine, histidine, isoleusine, leucine, lysine, methionine, phenylalanine, threonine, tryptophan, tyrosine, and valine may be included.

The fatty acids can be provided by natural oils, such as soybean oils, olive oils, coconut oils. The polyols can be propylene glycol, ethylene glycol, 1,3-butylene glycol or dipropylene glycol, $C_3$-$C_4$ ketones and $C_2$-$C_4$ aldehydes, and glycerin. The aqueous phase may consist essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, $C_3$-$C_4$ ketones and $C_2$-$C_4$ aldehydes, and glycerin.

The aqueous phase (water and optionally the water-miscible organic solvent) may be present in a content ranging from 1% to 98% by weight, relative to the total weight of the composition, optionally from 3% to 96%, from 40% to 95%, from 50% to 90%, from 60% to 90%, or from 70% to 85%.

Such an aqueous formulation can be used as skin toner, moisturizer or humectant to promote skin cell regeneration and prevent skin aging.

Optionally, the composition may be in a form of an emulsion or a cream formulation. It can contain emulsifying surfactants, present in particular in a proportion ranging from 2% to 30% by weight relative to the total weight of the composition, and better still from 5% to 15%. These surfactants may be chosen from among anionic and nonionic surfactants. Reference may be made to the document "Remington: The Science and Practice of Pharmacy," $20^{th}$ edition, 2000, pp. 285-287, for examples of anionic and nonionic surfactants.

Surfactants used in the composition according to aspects of the invention may be chosen from: nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, in particular polyoxyethylenated fatty esters of $C_1$-$C_6$ alkyl glucose, and mixtures thereof; anionic surfactants: $C_{16}$-$C_{30}$ fatty acids neutralized with amines, aqueous ammonia or alkaline salts, and mixtures thereof. According to aspects of the invention, surfactants which make it possible to obtain an oil-in-water or wax-in-water emulsion may be used.

Optionally, the composition according to aspects of the present invention may be in the form of an aqueous gel or a hydrogel formulation. The hydrogel formulation may include a thickening agent to thicken the liquid solution. Examples of thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition are preferably used.

The compositions according to aspects of the invention may further comprise an effective amount of a physiologically acceptable antioxidant selected from the group consisting of butylated p-cresol, butylated hydroquinone monomethyl ether, and a tocopherol. The antioxidant can be present in amounts of 0.005-5% by weight of the total composition.

The compositions according to aspects of the invention may further comprise natural or modified collagen, silk protein or soy protein. The protein can be present in amounts of from 0.01-10% by weight of the total composition.

In accordance with aspects of the invention, some compositions may be more or less fluid and may have the appearance of a white or colored cream, an ointment, a milk, a lotion, a serum, a paste, a mousse or a gel. They may be used as care products and/or as makeup products for the skin.

In known fashion, the compositions according to aspects of the invention may also contain additives and adjuvants that are common in cosmetics, such as hydrophilic or lipophilic gelling agents, preservatives, antioxidants, solvents, fragrances, fillers, pigments, odor absorbers and dyestuffs. The amounts of these various additives and adjuvants are those conventionally employed in the field under consideration, and range, for example, from 0.01% to 20% of the total weight of the composition. Depending on their nature, these additives and adjuvants may be introduced into the fatty phase or into the aqueous phase.

When the composition according to aspects of the invention is an emulsion, the proportion of the fatty phase advantageously ranges from 2% to 80% by weight and preferably from 5% to 50% by weight relative to the total weight of the composition. The fatty substances, emulsifiers and co-emulsifiers included in the composition in emulsion form are selected from among those conventionally formulated in the field under consideration. The emulsifier and co-emulsifier are preferably present in the composition in a proportion ranging from 0.3% to 30% by weight and preferably from 0.5% to 20% by weight relative to the total weight of the composition.

Exemplary fatty substances according to the invention include oils and especially mineral oils (liquid petroleum jelly), oils of plant origin (avocado oil, evening primrose oil, safflower oil, soybean oil, wheat germ oil, apricot kernel oil), oils of animal origin (lanolin), synthetic oils (perhydrosqualene), silicone oils (cyclomethicone) and fluoro oils (perfluoro polyethers). Fatty alcohols such as cetyl alcohol, fatty acids, waxes and gums and in particular silicone gums are also representative fatty substances.

Exemplary emulsifiers and co-emulsifiers according to the invention include fatty acid esters of polyethylene glycol, such as PEG-100 stearate, PEG-50 stearate and PEG-40 stearate; fatty acid esters of polyols, such as glyceryl stearate, sorbitan tristearate and oxyethylenated sorbitan stearates commercially available under the trademark Tween™20 or Tween™60, for example; and mixtures thereof.

Exemplary hydrophilic gelling agents may include in particular, carboxyvinyl polymers (carbomer), acrylic copolymers such as acrylate/alkyl acrylate copolymers, polyacrylamides, polysaccharides, natural gums and clays. Exemplary lipophilic gelling agents may include, in particular, modified clays, for example bentones, metal salts of fatty acids and hydrophobic silica.

Aspects of the present invention relate more particularly to a cosmetic regime or regimen for treating adverse signs of aging of the skin and/or a dull complexion and/or skin pigmentation disorders and/or skin dryness and/or sensitive skin, comprising topically applying the composition, formulated into a physiologically acceptable medium, onto the skin, for such period of time as required to elicit the desired cosmetic/therapeutic response.

By the expression "signs of aging of the skin" are intended wrinkles and fine lines, loss of firmness and/or elasticity of the skin, cutaneous atrophy, a more irregular skin grain with presence of dilated pores, loss of radiance of the skin, and/or pigmentary marks.

By the term "moisturizer" is intended:

(a) either a compound acting on the barrier function, in order to maintain the moisturization of the stratum corneum, or an occlusive compound. Examples include the ceramides, sphingoid-based compounds, lecithins, glycosphingolipids, phospholipids, cholesterol and derivatives thereof, phytosterols (stigmasterol, β-sitosterol or campesterol), essential fatty acids, 1,2-diacylglycerol, 4-chromanone, pentacyclic triterpenes, petroleum jelly and lanolin;

(b) or a compound that directly increases the water content of the stratum corneum, such as threalose and derivatives thereof, hyaluronic acid and derivatives thereof, glycerol, pentanediol, pidolates, amino acids (for examples serine, proline, glutamates, arginine), xylitol, urea, creatine, glucosamines, lactic acid, lactates, polyglyceryl acrylate, ectoin and derivatives thereof, chitosan, sugars, oligosaccharides and polysaccharides, cyclic carbonates, polyaspartate and derivates thereof, pyrrolidone-carboxylic acid and derivatives thereof, N-lauroyl-pyrrolidonecarboxylic acid, N-lauroyl-lysine and N-.alpha.-benzoyl-L-arginine;

(c) or a compound that activates the sebaceous glands, such as steroid derivatives (including DHEA) and vitamin D and derivatives thereof.

These compounds advantageously constitute from 0.001% to 30% and preferably from 0.01% to 20% of the total weight of the composition according to the invention.

According to aspects of the invention, compositions containing one or more of the above compounds are particularly suitable for preventing or treating the signs of aging of the skin, in particular loss of firmness and/or elasticity of the skin. Exemplary agents for stimulating the proliferation of fibroblasts that may be formulated into the compositions of the invention include plant proteins or polypeptides, extracts, especially of soybeans (for example an extract of soybean marketed by LSN under the trademark Eleseryl SH-VEG8® or marketed by Silab under the trademark Raffermine®); and plant hormones such as giberrellins and cytokinins.

According to aspects of the invention, compositions comprising these compounds are preferably used for preventing or treating the signs of aging of the skin.

Exemplary antimicrobial agents that may be formulated into the compositions according to aspects of the invention include 2,4,4'-trichloro-2'-hydroxydiphenyl ether (or triclosan), 3,4,4'-trichloro-banilide, phenoxyethanol, phenoxypropanol, phenoxy-isopropanol, hexamidine isethionate, metronidazole and its salts, micronazole and its salts, itraconazole, terconazole, econazole, ketoconazole, saperconazole, fluconazole, clotrimazole, butoconazole, oxiconazole, sulphaconazole, sulconazole, terbinafine, ciclopirox, ciclopiroxolamine, undecylenic acid and its salts, benzoyl peroxide, 3-hydroxybenzoic acid, 4-hydroxy-benzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanalide, octopirox, octoxyglycerine, octanoylglycine, caprylyl glycol, 10-hydroxy-2-decanoic acid, dichlorophenylimidazole dioxolane and its derivatives described in WO 93/18743, farnesol and phytosphingosines, and mixtures thereof.

The preferred antimicrobial agents are triclosan, phenoxyethanol, octoxyglycerine, octanoyl-glycine, 10-hydroxy-2-decanoic acid, caprylyl glycol, farnesol and azelaic acid.

By way of example, the antimicrobial agents may be formulated into the compositions according to aspects of the invention in amounts advantageously representing from 0.1% to 20% and preferably from 0.1% to 10% of the total weight of the composition.

By the term "tensioning agent" is intended a compound capable of exerting tension on the skin, the effect of which is to temporarily fade out irregularities on the skin's surface, such as wrinkles and fine lines.

Among the tensioning agents that may be formulated into the compositions according to aspects of the present invention, especially representative are:

(1) polyurethane lattices or acrylic-silicone lattices, in particular those described in US Published Patent Application No. 2002/0131948, such as a propylthio(polymethylacrylate), propylthio(polymethyl methacrylate) or propylthio(polymethacrylic acid) grafted polydimethylsiloxane, or alternatively a propylthio(polyisobutyl methacrylate) and propylthio(polymethacrylic acid) grafted polydimethylsiloxane. Such grafted silicone polymers are marketed by 3M under the trademark VS 80, VS 70 or LO21.

(2) soybean or wheat plant proteins, and/or (3) sodium magnesium silicates (Laponites).

According to aspects of the invention, compositions comprising the above tensioning agents are well suited for treating the signs of aging of the skin, in particular wrinkles and fine lines.

The free-radical scavengers that may be included in the compositions according to the invention comprise, other than certain anti-pollution agents indicated above, vitamin E and derivatives thereof such as tocopheryl acetate; bioflavonoids; coenzyme Q10 or ubiquinone; certain enzymes, for example, catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin.

According to aspects of the invention, compositions comprising the anti-pollution agents and/or free-radical scavengers indicated above are well suited for preventing or treating the signs of aging of the skin, in particular wrinkles, and loss of firmness and elasticity of the skin and dehydration. As a variant, these compositions are useful for preventing or treating a dull complexion.

The composition should also comprise a vehicle to enable the active ingredient to be conveyed to the skin in an appropriate dilution. The composition may be in a form of a liquid, suspension, emulsion, lotion, or cream.

The selection of a vehicle for the active ingredient(s) in compositions of the invention presents a wide range of possibilities depending on the required product form of the composition. Suitable vehicles can be classified as described hereinafter.

It should be explained that vehicles are substances which can act as diluents, dispersants, or solvents for the active ingredients and which therefore ensure that they can be applied to and distributed evenly over the skin at an appropriate concentration. A vehicle is preferably one which can aid penetration of the active ingredient into the skin, thus ensuring that the effectiveness of the active ingredient is prolonged because of improved properties. Compositions according to aspects of the invention can include water as a vehicle, and/or at least one cosmetically acceptable vehicle other than water.

Vehicles other than water that can be used in compositions according to aspects of the invention can include solids or liquids such as emollients, propellants, solvents, humectants, thickeners and powders. Examples of each of these types of vehicles, which can be used singly or as mixtures of one or more carriers, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, castor oil, acetylated lanolin alcohols, petroleum, mineral oil, butyl myristate, isostearic acid, palmitic acid, isopropyl linoleate, lauryl lactate, myristyl lactate, decyl oleate, myristyl, or myristate;

Propellants, such as trichlorofluoromethane, dichlorodifluoromethane, dichlorotetrafluorethane, monochlorodigluoromethane, trichlorotrifluorethane, propane, butane, isobutane, dimethyl ether, carbon dioxide, or nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, or tetrahydrofuran;

Humectants, such as glycerin, sorbitol, sodium 2-pyrrolidone-5-carboxylate, soluble collagen, dibutyl phthalate, or gelatin; and Powders, such as chalk, talc, fullers, earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, or ethylene glycol monostearate.

The amount of vehicle in the composition, including water if present, should preferably be sufficient to carry at least a portion of the active ingredient to the skin in an amount which is sufficient effectively to provide skin benefit. The amount of the vehicle can comprise the major portion of the composition, particularly where little or no other ingredients are present in the composition.

The composition will accordingly comprise from 15 to 99.989% and preferably from 50 to 99.5% by weight of the vehicle or vehicles.

The composition according to aspects of the invention can contain ingredients other than those already mentioned, depending on the form of the intended product. It is, for example, possible to include antiseptics, preservatives, antioxidants, emulsifiers, coloring agents, and detergents, some of which are described in detail above.

The composition according to aspects of the invention can also be employed as a vehicle for a wide variety of cosmetically or pharmaceutically active ingredients, particularly ingredients which have some beneficial effect when applied to the skin.

The composition thus provides a means whereby such active ingredients can be diluted, dispersed, conveyed to, and distributed on the skin surface at an appropriate concentration.

The invention also provides a kit for skin care or treatment, comprising: a vessel containing the inventive composition, optionally further comprising instructions on how to use the inventive composition.

The inventive composition may also be embedded in a mask for the face or the body. The mask may comprise a backing sheet containing the inventive composition serving to exert a specific action on the skin. The backing sheet may be in a dry or web state, preferably stretchable at least in the wet state, in order to enable the mask to be adapted to fit the shape of the face or of the portion of the body to be treated. The backing sheet may be made of paper, fabric, cloth, or a polymeric material.

Aspects of the invention also provide a process for the preparation of a cosmetic composition for topical application to skin which comprises mixing an active ingredient, as herein defined, with a suitable vehicle to provide a concentration of from 0.001% to 0.5%.

The compositions according to aspects of the invention can be formulated as liquids, for example as a lotion or milk for use in conjunction with an applicator such as a roll-ball applicator, or a spray device such as an aerosol can containing propellant, or a container fitted with a pump to dispense the liquid product. Alternatively, the compositions according to aspects of the invention can be solid or semi-solid, for example sticks, creams or gels, for use in conjunction with a suitable applicator, or simply a tube, bottle or lidded jar, or as a liquid-impregnated fabric, such as a tissue wipe.

Preferably the composition is an aqueous emulsion and this can be a water-in-oil emulsion, or an oil-in-water emulsion. In one aspect, a particularly important composition for the invention is an aqueous fat emulsion in which the aqueous phase of the emulsion acts as a carrier.

Pharmaceutical compositions for topical application are particularly important in accordance with aspects of the invention, because skin condition is dependent on the presence of essential fatty acids. Such compositions can be liquid or plastic: liquid compositions include oils comprising the inventive composition with or without additional carrier oil; lotions, such as a solution in a physiologically acceptable solvent of an ester of the invention in free or derivative form, for instance an aqueous solution or an aqueous emulsion of the ester; and creams and ointments, such as a plastic dispersion of the ester in free or derivative form in a suitable carrier, for instance an ointment base. Such compositions are useful in the prevention and cure of skin damage caused by contact with detergents, and in treating environmental trauma due to weathering, sunburn, burns of other types and in reducing bacterial activity on the skin.

Aspects of the invention accordingly also provide a closed container containing a cosmetic composition as herein defined.

Compositions according to aspects of the invention are intended especially for topical application to human skin, in particular when the skin surface has become excessively dry, fissured, eroded or otherwise damaged.

In one aspect, the invention accordingly also includes a process of topical administration of the composition of the invention to human subjects suffering from or liable to suffer from excessively dry, fissured, eroded or otherwise damaged skin and other skin disorders. The dosage rate will depend on the condition to be treated as well as the route of administration. Local skin symptoms may require one or more applications of the composition.

Aspects of the invention also provide for the use of an active ingredient, as herein defined, in the topical treatment of skin disorders.

The effectiveness of the inventive compositions on the promotion or restoration of the skin barrier function may be evaluated by using experimental animal models or tested on human subjects.

Aspects of the present invention also provides a method for treating undesirable or pathological skin conditions of a mammal. The method comprises: topically applying to the skin of the mammal a composition in a physiologically acceptable medium for such period of time as required to elicit the desired cosmetic/therapeutic response. Examples of the undesirable skin condition include, but are not limited to, adverse signs of aging of the skin, a dull complexion, skin pigmentation disorders, skin dryness, and sensitive skin. Examples of pathological skin condition include, but are not limited to, the dermatologic diseases linked to a keratinization disorder (differentiation-proliferation), inflammation and/or immunoallergy.

Each citation indicated above, whether of the open literature, patent, patent application, or otherwise, is hereby expressly incorporated by reference.

In order to further illustrate aspects of the present invention and the advantages thereof, the following specific examples are given, it being understood that same are intended only as illustrative and in nowise limitative.

In said examples to follow, all parts and percentages are given by weight.

EXAMPLES

Example 1: Lotion

This example describes an embodiment of the compositions according to the invention, which is a water-oil emulsion and may be used as skin lotion. The ingredients of the lotion are listed as follows.

| | |
|---|---|
| Cetyl alcohol | 1.20% |
| Mineral Oil | 2.00% |
| PEG-100 stearate | 3.00% |
| Glyceryl monostearate | 4.00% |
| Soybean Oil | 1.90% |
| Water | 83.20% |
| Calcium chloride | 0.30% |
| Magnesium chloride | 0.40% |
| Sodium chloride | 0.50% |
| Glycerin | 2.10% |
| Collagen amino acids | 0.50% |
| Preservatives | 0.90% |

This solution contains combination of ions with amino acids and glycerin. Briefly, the solution in this example was prepared according to the following procedure. Sodium chloride, magnesium chloride and calcium chloride were added in a consecutive order while stirring until each one was totally dissolved. Amino acids and glycerin and the preservative were then added.

Example 2: Cream

This example describes an embodiment of the compositions according to the invention, which is a water-oil emulsion and may be used as skin care cream. The ingredients of the emulsion (designated as Cream Formulation I) are listed as follows.

| | |
|---|---|
| Beeswax | 3.20% |
| Emulsifying Wax | 5.90% |
| Mineral Oil | 0.90% |
| Soybean Oil | 1.00% |
| Water | 83.20% |
| Calcium chloride | 0.50% |
| Magnesium chloride | 0.40% |
| Sodium chloride | 0.40% |
| Glycerin | 2.90% |
| Silk amino acids | 0.70% |
| Preservatives | 0.90% |
| Fragrance | q.s. |

Example 3: In Vivo Study to Assess Effects of Inventive Lotion and Cream on Human Subjects with Known Condition of Dry Skin This example describes an in vivo study undertaken to assess the effect of the Lotion formulation described in Example 1 and Cream Formulation in Example 2 on subjects with a known condition of dry and aging skin.

1) Materials and Methods:

A total of 10 subjects, male and female aged 40 to 70 years, with minimal to mild dry skin symptoms in the facial area, participated in the study. Each subject was given a set of toner formulation described in Example 1 and Cream Formulation in Example 2 to be applied to the symptomatic area twice daily for two weeks. The daily self-evaluation was documented on the score of results on the Clinical Research Form (CRF). On week 2 the CRF was collected from the subjects for data analysis.

Safety evaluation: Safety was assessed from vital signs, signs and symptoms of applied skin, and reported adverse experiences.

Efficacy evaluation: To determine the efficacy, the time to reach no clinical sign of dry skin and fine lines was used as a parameter.

2) Results:

Based on basic scoring for scaling, all subjects had reported conditions that fell below the dry skin score of 2, which is mild; fine, flaky scale predominated; and reduction of fine lines. The average score was 1.28 for 10 subjects. Median age was 54.5 years old. On safety evaluation, all subjects reported no adverse effects during the period of the study.

3) Conclusion

The study demonstrates the safety and efficacy of the inventive lotion and cream to alleviate the symptoms of dry skin in minimal to mild cases and the reduction of fine lines. No adverse reaction was reported.

What is claimed is:

1. A skin care composition, comprising:
   chloride salts including calcium chloride, magnesium chloride, and sodium chloride, wherein the composition comprises about 1.7% w/w of sodium, calcium, magnesium, and zinc ions, based on the total weight of the composition in a physiologically acceptable medium selected from the group consisting of lotion, gel, hydrogel, and cream, and in the presence of about 0.5% of collagen amino acids and about 0.05-3% of fatty acids produced from oils selected from the group consisting of mineral oil, soybean oil, olive oil, and coconut oil, with 0.1-5% polyols selected from the group consisting of propylene glycol, ethylene glycol, 1,3-butylene glycol, dipropylene glycol, and glycerin.

2. The composition according to claim 1, wherein the ions are in solubilized form from the chloride salts.

3. The composition according to claim 1, wherein the collagen amino acids are in an aqueous solution.

4. The composition according to claim 1, wherein the composition is in a form of an emulsion.

5. The composition according to claim 1, wherein the composition further comprises an emulsifying surfactant at 2% to 30% by weight relative to the total weight of the composition.

6. The composition according to claim 5, wherein the emulsifying surfactant is a nonionic surfactant selected from the group consisting of: fatty alcohols, polyethoxylated stearyl or cetylstearyl alcohol, alkylglucose esters, and mixtures thereof.

7. The composition according to claim 5, wherein the emulsifying surfactant is an anionic surfactant selected from the group consisting of: $C_{16}$-$C_{30}$ fatty acids alkaline salts, and mixtures thereof.

* * * * *